United States Patent [19]

Oda et al.

[11] Patent Number: 5,091,191

[45] Date of Patent: Feb. 25, 1992

[54] PHARMACEUTICAL COMPOSITION WITH IMPROVED DISSOLUTION PROPERTY

[75] Inventors: Minoru Oda, Nakatsu; Shigemi Kino, Chikujo; Kenji Ogawa, Chikujo; Takako Shiotsuki, Chikujo, all of Japan

[73] Assignee: Yoshitomi Pharmaceutical Industries, Ltd., Osaka, Japan

[21] Appl. No.: 415,356

[22] PCT Filed: Jan. 31, 1989

[86] PCT No.: PCT/JP89/00100

§ 371 Date: Sep. 25, 1989

§ 102(e) Date: Sep. 25, 1989

[87] PCT Pub. No.: WO89/06959

PCT Pub. Date: Aug. 10, 1989

[30] Foreign Application Priority Data

Feb. 3, 1988 [JP] Japan .................................. 63-23250

[51] Int. Cl.$^5$ ..................... A61K 31/41; A61K 47/26; A61K 47/38; A61K 9/16
[52] U.S. Cl. .................................... 514/399; 424/475; 424/479; 424/457; 424/466; 424/486; 424/488; 424/501
[58] Field of Search ............... 424/499, 457, 465, 466, 424/461, 462, 475, 479; 514/396

[56] References Cited

U.S. PATENT DOCUMENTS 4,661,603 4/1987 Tsuruda et al. ..................... 548/346
4,737,506 4/1988 Shimizu et al. ..................... 514/332

FOREIGN PATENT DOCUMENTS

0110996A1 6/1984 European Pat. Off. .
0164588A3 3/1986 European Pat. Off. .
119425 5/1988 Japan .

Primary Examiner—Thurman K. Page
Assistant Examiner—E. J. Webman
Attorney, Agent, or Firm—Wenderoth, Lind & Ponack

[57] ABSTRACT

A pharmaceutical composition of the active agent sodium 4-[α-hydroxy-5-(1-imidazolyl)-2-methylbenzyl]-3,5-dimethylbenzoate (a thromboxane synthetase inhibitor for treatment of diseases such as thrombosis and asthma) or its optical isomer or its hydrate with an improved dissolution property, which comprises D-mannitol and/or sodium hydrogencarbonate and at least one water-soluble polymer.

The pharmaceutical composition is such that the dissolution of the above-mentioned active agent is free from pH dependency in the digestive tract including the stomach.

2 Claims, 4 Drawing Sheets

DISSOLUTION OF FINE GRANULES OF EXAMPLE 1 INTO ACETATE BUFFER SOLUTION, pH4.0

PHARMACEUTICAL COMPOSITION WITH IMPROVED DISSOLUTION PROPERTY

TECHNICAL FIELD

This invention relates to pharmaceutical compositions with improved dissolution property of sodium 4-[α-hydroxy-5-(1-imidazolyl)-2-methylbenzyl]-3,5-dimethylbenzoate or its optical isomer or its hydrate which is useful as a thromboxane synthetase-inhibiting medicine.

BACKGROUND ART

In the specification of U.S. Pat. No. 4661603, it is disclosed that sodium 4-[α-hydroxy-5-(1-imidazolyl)-2-methylbenzyl]-3,5-dimethylbenzoate or its optical isomer or its hydrate (hereinafter referred to generally as "the Compound" including the corresponding hydrate) is useful as a thromboxane synthetase-inhibitor in a therapeutic medicament for diseases such as thrombosis and asthma, and can be formed into oral preparations such as tablets or into injections. In said U.S. Patent, there are also disclosed pharmaceutical formulation examples containing lactose, starch, fine crystalline cellulose, talc and magnesium stearate as the carriers or excipients.

Since the Compound is a sodium salt in the carboxyl group moiety, its solubility is lowered under weakly acid to neutral conditions (in the range of about pH 3 to about pH 7) as shown in FIG. 1. Therefore, pharmaceutical compositions obtained by such a conventional means as described in the above-mentioned U.S. Patent specification, for example, by adding lactose, corn starch and the like to the Compound, granulating the mixture, adding talc, magnesium stearate and the like thereto and compressing for forming, have a pretty inferior dissolution property in the weakly acid dissolution test medium, e.g. 0.1 M acetate buffer solution (pH 4.0). This is a reflection of the property of the Compound per se, as shown in FIG. 2.

It is widely known that when a compound having such dissolution property which depends on the pH of the dissolution test medium or a pharmaceutical composition thereof is administered to a human, the pH in the stomach influences the absorption rate and the like.

On the other hand, it is also well known that the pH in the stomach of aged people quite frequently ranges from weakly acid area to neutral area. Thus, in view of the fact that patients to be treated with the Compound are often aged people, pharmaceutical improvement of the preparations is strongly demanded.

Accordingly, in order to assure uniform pharmaceutical effects to the patients, there has been desired the development of a pharmaceutical composition wherein the dissolution of the Compound is free from any dependency on the pH of the digestive tract including the stomach. That is, it is required to obtain a pharmaceutical composition with improved pH-dependent dissolution property of the Compound by adding additives in combination, which do not exhibit any particular pharmacological actions by themselves and are harmless.

In general, as the methods for improving dissolution of sparingly-soluble medicaments, there are known (1) a method of finely-powdering, (2) a method of forming a molecular compound (3) a method of forming a solid dispersion (4) a method of converting into a soluble derivative and the like.

Since the Compound is in the form of a sodium salt, even if it was treated by a known method belonging to the abovementioned (1), the corresponding free acid was produced through chemical reaction when added to a weakly acid solution. Thus, there was not found any dissolution-improving effect by the method.

According to the methods belonging to the above methods (2) and (3), no effect can be expected unless the additives are added in a not less than 3 to 4 times larger amount relative to the amount of the bulk of the Compound. Thus, they pose problems when put to practical use in view of the clinical dosage of the Compound. Furthermore, the above method (4) cannot be adopted in case where it is required to use the Compound per se.

DISCLOSURE OF THE INVENTION

The object of this invention is to provide pharmaceutical compositions with improved dissolution of the Compound.

This invention relates to a pharmaceutical composition of sodium 4-[c-hydroxy-5-(1-imidazolyl)-2-methylbenzyl]-3,5-dimethylbenzoate or its optical isomer or its hydrate, which is characterized by containing D-mannitol and/or sodium hydrogencarbonate and at least one water-soluble polymer compound.

DETAILED DESCRIPTION OF THE INVENTION

Figure 1:
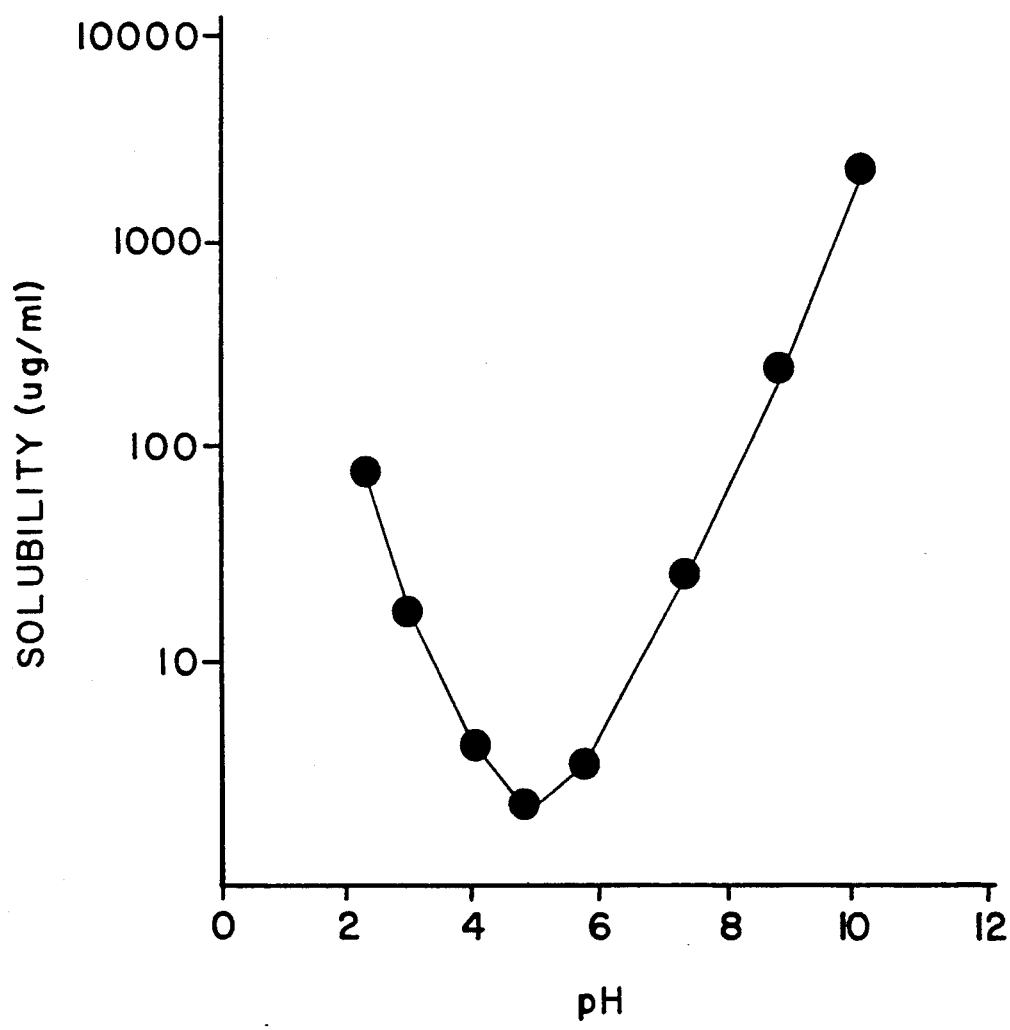
FIG. 1 is a graph showing the solubility of the Compound at different ph valves.

As the preferred water-soluble polymer compounds to be used in the present invention, mention can be made of one or more species selected from among hydroxypropylcellulose, hydroxypropylmethylcellulose, methylcellulose and polyvinylpyrrolidone.

The preferable mode of the present invention is a pharmaceutical composition of sodium 4-[α-hydroxy-5-(1-imidazolyl)-2-methylbenzyl]-3,5-dimethylbenzoate or its optical isomer or its hydrate, which comprises additives belonging to a group of D-mannitol and/or sodium hydrogencarbonate and to a group of hydroxypropylcellulose and/or hydroxypropylmethylcellulose.

The effective ingredient, sodium 4-[α-hydroxy-5-(1-imidazolyl)-2-methylbenzyl]-3,5-dimethylbenzoate, exists in the form of 2 hydrate and is a crystal having a m.p. of 271°–285° C. This compound has an asymmetric carbon, and thus it has optical isomers, all of which are encompassed in the present invention. The optical rotation $\{[\alpha]^{21}_D$ value (C=1.0, water)$\}$ of the (−) compound having a the sodium salt is −149.5° and that of the (+) compound of the sodium salt is +147.2°.

More specifically, the present invention relates to pharmaceutical compositions with improved dissolution property, which is characterized by selecting (a) An additive capable of maintaining the condition of the supersaturated solution of the Compound for a long time even in a weakly acid solution and (b) An additive which enables the composition to be rapidly disintegrated and dispersed, and comprising (c) An excipient possessing a dissolution-promoting effect in cooperation with the characteristics of (a) and (b).

Detailed explanation of the foregoing is given below.

(1) It was found that by adding at least one water-soluble polymer compound such as polyvinylpyrrolidone, hydroxypropylcellulose or hydroxypropylmethylcellulose to the Compound, the crystallization (of the free acid of the Compound) in a weakly acid solution is suppressed and the supersaturated solution condition is maintained for a long period. This fact means that the solubility of the Compound or the free acid corresponding thereto in the body after being administered is improved, which further implies a high possibility of improvement in the bioavailability (hereinafter referred to as BA).

(2) In view of the characteristics of the Compound, it is essential that the pharmaceutical composition is rapidly disintegrated and dispersed in the body for the purpose of improving BA, whereby the active ingredient is dissolved. It was found that for this purpose, sodium hydrogencarbonate was very effective.

(3) In the pharmaceutical preparation, excipients are usually added to the bulk of the active ingredient and the mixture is formulated into a form of a certain size for the sake of convenience of administration, and for this purpose, a combination of lactose, starch, crystalline cellulose and the like which do not exhibit any pharmacological actions and are harmless has been conventionally used. After studies on a variety of excipients, D-mannitol was selected, because it does not damage the stability of the Compound and has an excellent dissolution-improving effect.

(4) As the result of additional studies, it was also found that when hydroxypropylcellulose and/or hydroxypropylmethylcellulose were (was) selected from among the compounds as described above in (1), and added in combination with, sodium hydrogencarbonate as described above in (2) and/or D-mannitol as described above in (3) to the Compound, and the resultant mixture was formed into preparations, the obtained preparations exhibited improved dissolution property as compared with the preparations obtained by separately adding the above-mentioned compounds. This complex effect was so remarkable that the effect could be considered not so much an additive one as a synergistic one.

Additives usable for pharmaceutical preparations such as fillers and lubricants can be added to the pharmaceutical composition of the present invention, which can be formulated into dosage forms such as tablets (including sugar-coated tablets and film-coated tablets), fine granules and capsules.

The content of the Compound in the pharmaceutical compositions of the present invention is preferably 1 - 50% by weight. The proportion of D-mannitol and/or sodium hydrogencarbonate to the water-soluble polymer compound(s) such as hydroxypropylcellulose and/or hydroxypropylmethylcellulose is preferably in the range of 1:1 to 200:1, more preferably 20:1 to 200:1.

Below, the present invention is described by illustrating Reference Example and Examples, but the present invention is not limited thereto. The Compound used therein is in the form of 2 hydrate.

REFERENCE EXAMPLE 1

| | |
|---|---|
| The Compound | 50.0 mg |
| Lactose | 40.0 mg |
| Corn starch | 25.5 mg |
| Talc | 4.0 mg |
| Magnesium stearate | 0.5 mg |

Figure 2:
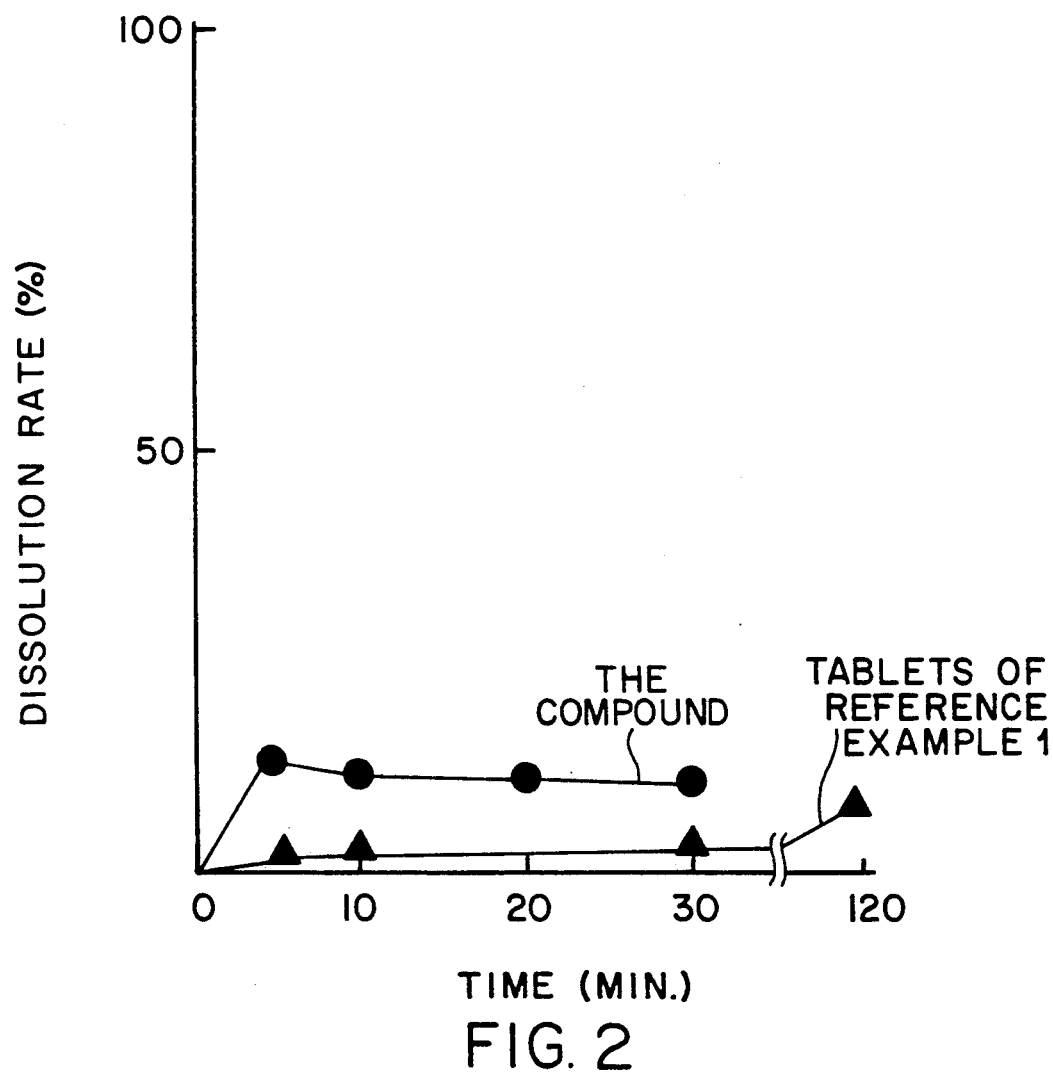
FIGS. 2, 3 and 4 are the graphs showing the dissolution test results of the Compound and the tablets of Reference Example 1, the fine granules of Example 1 and the tablets of Example 2, respectively.

A portion of the corn starch was prepared into a paste, which was kneaded with a mixture of the Compound, lactose and corn starch, and the kneaded mixture was granulated and dried at 50° C. After the granulated preparation was passed through a sieve of 24 mesh, talc and magnesium stearate were added thereto. The mixture was compressed into tablets of 120 mg per tablet with a rotary tableting machine (Kikusui Manufacturer). For these tablets and the Compound per se, the dissolution test was conducted with the use of acetate buffer solution of pH 4.0 in accordance with the 2nd method of the dissolution test of the Japan Pharmacopoeia (900 ml, 37° C., 100 rpm), and the results are shown in FIG. 2.

In the Figure, -●-●- shows the result of the dissolution test of the Compound and -▲-▲- shows that of the tablets of Reference Example 1.

EXAMPLE 1

| [Formulation 1] | |
|---|---|
| The Compound | 10% |
| D-Mannitol | 90% |

The Compound was mixed with D-mannitol, and water was added thereto. The mixture was kneaded, granulated and dried at 50° C. The granulated preparation was passed through a sieve of 32 mesh to give fine granules.

| [Formulation 2] | |
|---|---|
| The Compound | 10.0% |
| D-Mannitol | 88.5% |
| Hydroxypropylcellulose | 1.5% |

The Compound and D-mannitol were mixed, and an aqueous solution of hydroxypropylcellulose was added to the mixture. The mixture was kneaded and granulated, and the same procedure as in Formulation 1 was followed to give fine granules.

| [Formulation 3] | |
|---|---|
| The Compound | 10.0% |
| Corn starch | 88.5% |
| Hydroxypropylcellulose | 1.5% |

The Compound was mixed with corn starch, and the same procedure as in Formulation 2 was followed to give fine granules.

| [Formulation 4] | |
|---|---|
| The Compound | 10.0% |
| D-Mannitol | 85.5% |
| Sodium hydrogencarbonate | 3.0% |
| Hydroxypropylcellulose | 1.5% |

The Compound, D-mannitol and sodium hydrogencarbonate were mixed and the same procedure as in Formulation 2 was followed to give fine granules.

Figure 3:
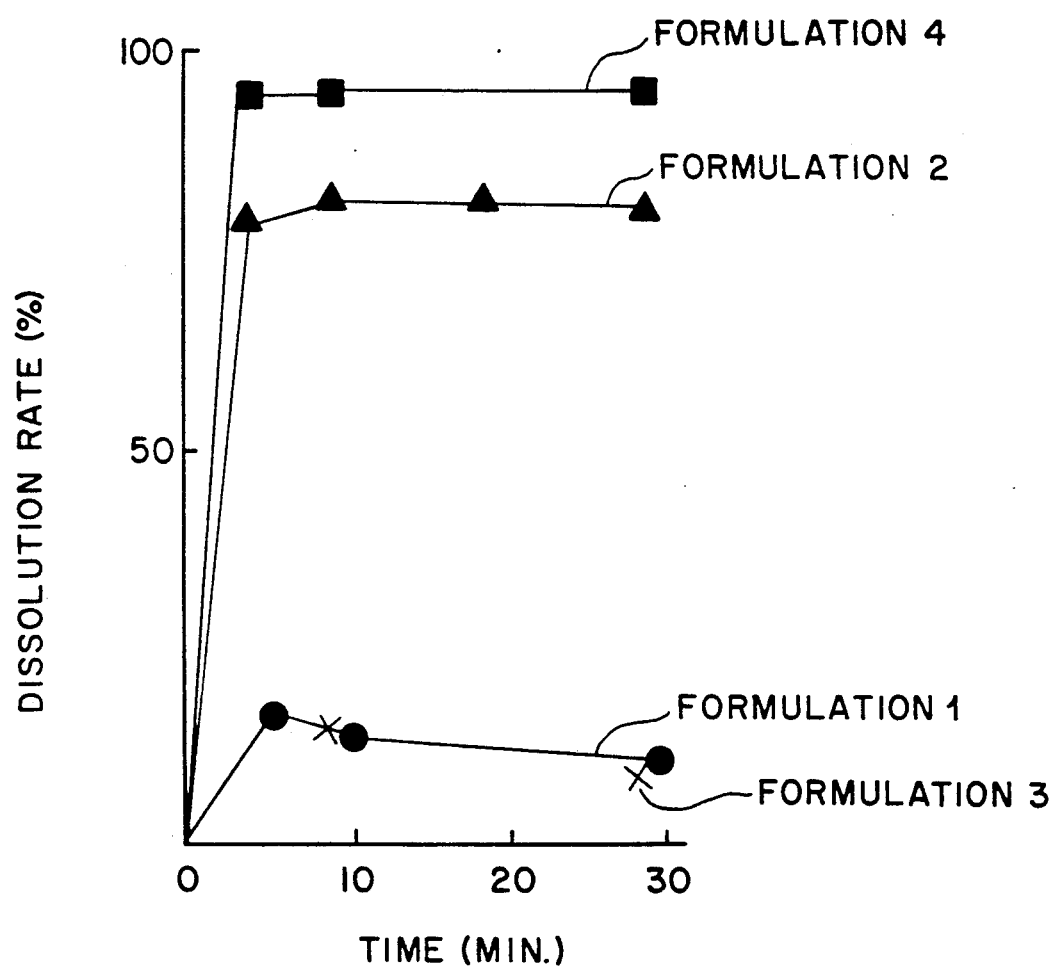

For Formulations 1-4, the dissolution test was carried out with the use of acetate buffer solution of pH 4.0 in accordance with the 2nd method (900 ml, 37° C., 100 rpm) of the dissolution test of the Japan Pharmacopoeia and the results are shown in FIG. 3. In the Figure, -●-●-, -▲-▲-, -X-X- and -■-■-, show the results of the dissolution test for the Formulations 1 to 4 respectively.

From the foregoing results, it was found that by the combination of D-mannitol, sodium hydrogencarbonate and watersoluble polymer compounds, the dissolution of the Compound was considerably improved and that such effects were not the result of a mere addition of individial effects of D-mannitol, sodium hydrogencarbonate and hydroxypropylcellulose but of total synergistic action brought about by the combination of them.

EXAMPLE 2

| The Compound | 50.0 mg |
|---|---|
| D-Mannitol | 70.5 mg |
| Corn starch | 16.0 mg |
| Sodium hydrogencarbonate | 15.0 mg |
| Hydroxypropylcellulose | 3.0 mg |
| Talc | 5.0 mg |
| Magnesium stearate | 0.5 mg |

The Compound, D-mannitol, corn starch and sodium hydrogencarbonate were mixed, and an aqueous solution of hydroxypropylmethylcellulose was sprayed to the mixture, and the mixture was granulated by fluidization. After the granulated preparation was passed through a sieve of 24 mesh, talc and magnesium stearate were added to the granules, and the mixture was compressed into tablets of 160 mg per tablet with a rotary tableting machine (Kikusui Manufacturer). These tablets were film-coated with 6 mg per tablet with hydroxypropylmethylcellulose film-coating base.

Figure 4:
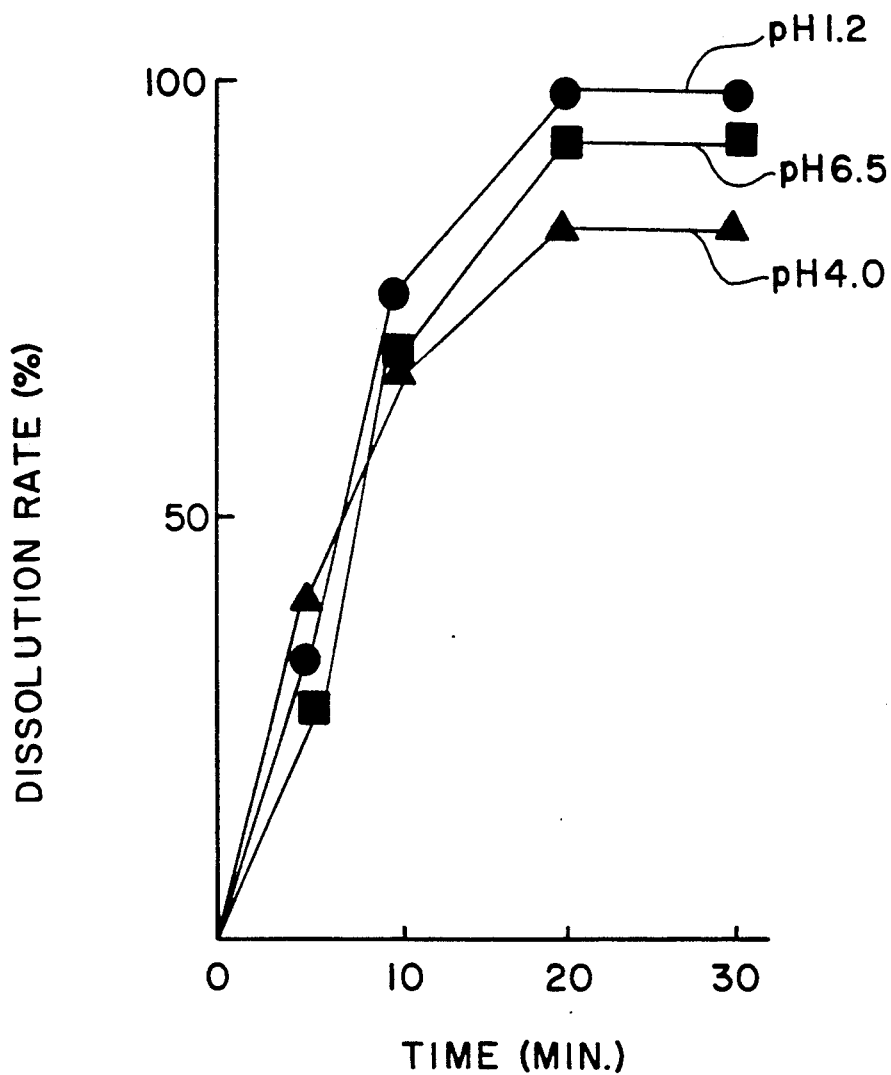

For the thus-obtained tablets, the dissolution test was conducted with the use of a buffer solution of pH 4.0 in the same manner as in Example 1. The results are, as shown in FIG. 4, that the tablets showed improved dissolution property. Besides, the dissolution in the solutions of pH 1.2 (the first fluid in the disintegration test method of the Japan Pharmacopoeia) and in phosphate buffer of pH 6.5 was rapid, which showed that the tablet compositions according to the present invention have a dissolution property free from pH dependency.

EXAMPLE 3

In accordance with the following formulation, fine granules were prepared in the same manner as in Example 1.

| The Compound | 10% |
|---|---|
| D-Mannitol | 89.5% |
| Hydroxypropylcellulose | 0.5% |

EXAMPLE 4

In accordance with the following formulation, the tablets of 120 mg per tablet were prepared in the same manner as in Example 1.

| The Compound | 50.0 mg |
|---|---|
| D-Mannitol | 30.0 mg |
| Corn starch | 19.0 mg |
| Sodium hydrogencarbonate | 15.0 mg |
| Hydroxypropylmethylcellulose | 1.5 mg |
| Talc | 4.0 mg |
| Magnesium stearate | 0.5 mg |

EXAMPLE 5

In accordance with the following formulation, fine granules were prepared in the same manner as in Example 2.

| The Compound [(−) compound] | 5% |
|---|---|
| D-Mannitol | 92% |
| Hydroxypropylmethylcellulose | 3% |

As explained in the specification, especially in the Examples, by adding D-mannitol and/or sodium hydrogen carbonate and a water-soluble polymer compound (preferably one or more species selected from among hydroxypropylcellulose, hydroxypropylmethylcellulose, methylcellulose and polyvinylpyrrolidone, more preferably hydroxypropylcellulose and/or hydroxypropylmethylcellulose) to sodium 4-[α-hydroxy-5-(1-imidazolyl)-2-methylbenzyl]-3,5-dimethylbenzoate or its optical isomer or its hydrate, a pharmaceutical composition with an improved dissolution property can be obtained.

The present invention has been properly and sufficiently explained in the foregoing specification including Examples, which can be changed or modified within the spirit and scope of the present invention.

We claim:
1. A pharmaceutical composition which comprises 1–50% by weight of sodium 4-[α-hydroxy-5-(1-imidazolyl)-2-methylbenzyl]-3,5-dimethylbenzoate, or its optical isomer, or its hydrate,
an additive selected from the group consisting of D-mannitol and a mixture of D-mannitol and sodium bicarbonate, and
at least one water-soluble polymer compound selected from the group consisting of hydroxypropylcellulose, hydroxypropylmethylcellulose, methylcellulose and polyvinylpyrrolidone,
wherein the proportion of D-mannitol or a mixture of D-mannitol and sodium bicarbonate to the water-soluble polymer is in the range of 20:1 to 200:1.
2. The composition according to claim 1, wherein said at least one water-soluble polymer is selected from the group consisting of hydroxypropylcellulose and hydroxypropylmethylcellulose.

* * * * *